(12) United States Patent
Bonn

(10) Patent No.: US 12,295,636 B2
(45) Date of Patent: May 13, 2025

(54) GAS-ENHANCED ENERGY-BASED SURGICAL INSTRUMENT, SYSTEM, AND METHOD FOR MINIMALLY-INVASIVE SURGICAL PROCEDURES

(71) Applicant: Covidien LP, Mansfield, MA (US)

(72) Inventor: Kenlyn S. Bonn, Lafayette, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/120,113

(22) Filed: Mar. 10, 2023

(65) Prior Publication Data

US 2023/0225780 A1 Jul. 20, 2023

Related U.S. Application Data

(63) Continuation of application No. 16/777,101, filed on Jan. 30, 2020, now abandoned.
(Continued)

(51) Int. Cl.
*A61B 18/14* (2006.01)
*A61B 17/00* (2006.01)
(Continued)

(52) U.S. Cl.
CPC .. *A61B 18/042* (2013.01); *A61B 2017/00424* (2013.01); *A61B 2018/00077* (2013.01);
(Continued)

(58) Field of Classification Search
CPC ... A61B 18/042; A61B 18/1482; A61B 18/14; A61B 2218/005; A61B 2218/006;
(Continued)

(56) References Cited

U.S. PATENT DOCUMENTS 5,199,944 A 4/1993 Cosmescu
5,423,807 A * 6/1995 Milder ............... A61M 25/0158
607/105

(Continued)

FOREIGN PATENT DOCUMENTS

DE 102012110889 A1 5/2014
WO 2007123565 A1 11/2007

OTHER PUBLICATIONS

Extended European Search Report issued in corresponding European Application No. 20155565.3 dated Jun. 23, 2020, 9 pages.

*Primary Examiner* — Thomas A Giuliani
*Assistant Examiner* — Abigail M Ziegler
(74) *Attorney, Agent, or Firm* — Carter, DeLuca & Farrell LLP

(57) ABSTRACT

A surgical instrument includes a housing, an elongated shaft assembly extending from the housing, and an end effector extending from the elongated shaft assembly. An inner shaft of the assembly defines proximal and distal portions and a longitudinal lumen. The proximal portion inhibits passage of gas while the distal portion permits passage of gas. An intermediate collar is disposed about the inner shaft between the proximal and distal portions. An outer sleeve of the assembly is disposed about the inner shaft and the intermediate collar to define a proximal area therebetween proximally of the intermediate collar and a distal annular area therebetween distally of the intermediate collar. The outer sleeve includes a proximal portion surrounding the proximal annular area and a distal portion surrounding the distal annular area. The proximal portion permits passage of gas while the distal portion inhibits passage of gas.

20 Claims, 6 Drawing Sheets

Related U.S. Application Data

(60) Provisional application No. 62/801,151, filed on Feb. 5, 2019, provisional application No. 62/801,153, filed on Feb. 5, 2019.

(51) Int. Cl.
*A61B 18/04* (2006.01)
*A61B 18/00* (2006.01)

(52) U.S. Cl.
CPC ..... *A61B 2018/00101* (2013.01); *A61B 18/14* (2013.01); *A61B 2018/1422* (2013.01); *A61B 18/1482* (2013.01); *A61B 2218/002* (2013.01); *A61B 2218/005* (2013.01); *A61B 2218/007* (2013.01)

(58) Field of Classification Search
CPC ........ A61B 2218/007; A61B 2218/008; A61B 2018/0256; A61B 2018/048
See application file for complete search history.

(56) References Cited

U.S. PATENT DOCUMENTS

| | | | |
|---|---|---|---|
| 5,669,907 A | 9/1997 | Platt, Jr. et al. | |
| 6,213,999 B1 | 4/2001 | Platt, Jr. et al. | |
| 6,241,700 B1 | 6/2001 | Leukanech | |
| 7,572,257 B2 | 8/2009 | Whayne et al. | |
| 7,988,656 B2 | 8/2011 | Uesugi et al. | |
| 8,323,279 B2* | 12/2012 | Dahla | A61B 18/1402 606/41 |
| 9,028,490 B2 | 5/2015 | Heard et al. | |
| 2005/0209578 A1 | 9/2005 | Christian Evans et al. | |
| 2005/0222534 A1 | 10/2005 | Jesugi et al. | |
| 2007/0208335 A1* | 9/2007 | Woloszko | A61B 18/148 606/41 |
| 2012/0172874 A1* | 7/2012 | Fischer | A61B 18/042 606/49 |
| 2012/0184897 A1 | 7/2012 | Poll | |
| 2013/0072950 A1 | 3/2013 | Ross et al. | |
| 2014/0200581 A1 | 7/2014 | Aluru et al. | |
| 2014/0257273 A1* | 9/2014 | Cosmescu | A61B 18/042 606/37 |
| 2014/0371667 A1 | 12/2014 | Kasuya | |
| 2016/0206361 A1* | 7/2016 | Jadhav | A61B 18/08 |
| 2017/0106199 A1 | 4/2017 | Woolford et al. | |
| 2017/0128127 A1 | 5/2017 | Skalnyi | |
| 2017/0360494 A1* | 12/2017 | Saadat | G01M 3/24 |
| 2018/0221598 A1 | 8/2018 | Silver | |
| 2018/0263550 A1 | 9/2018 | Filloux et al. | |
| 2019/0021782 A1* | 1/2019 | Segit | A61B 18/14 |
| 2019/0274726 A1* | 9/2019 | Beaven | A61M 19/00 |
| 2020/0222104 A1* | 7/2020 | Toth | A61B 18/1206 |
| 2021/0204994 A1* | 7/2021 | Kim | A61B 18/082 |
| 2021/0290864 A1 | 9/2021 | Yamaoka et al. | |
| 2021/0402108 A1 | 12/2021 | Spence et al. | |

* cited by examiner

GAS-ENHANCED ENERGY-BASED SURGICAL INSTRUMENT, SYSTEM, AND METHOD FOR MINIMALLY-INVASIVE SURGICAL PROCEDURES

CROSS-REFERENCE TO RELATED APPLICATIONS

This application is a continuation of U.S. patent application Ser. No. 16/777,101, filed on Jan. 30, 2020, which claims the benefit of U.S. Provisional Patent Application Nos. 62/801,151 and 62/801,153, both filed on Feb. 5, 2019. The entire contents of each of the above applications are hereby incorporated herein by reference.

BACKGROUND

Technical Field

The present disclosure relates to surgical instruments, systems, and methods and, more particularly, to gas-enhanced energy-based surgical instruments, systems, and methods for use in minimally-invasive surgical procedures.

Background of Related Art

In minimally-invasive surgical procedures, operations are carried out within an internal body cavity through small entrance openings in the body. The entrance openings may be natural passageways of the body or may be surgically created, for example, by making a small incision into which a cannula is inserted. However, the restricted access provided by minimally-invasive openings (natural passageways and/or surgically created openings) presents challenges with respect to maneuverability and visualization. Thus, in many minimally-invasive surgical procedures, the internal body cavity is insufflated with a gas to distend and separate the cavity wall from underlying tissue(s), thus improving maneuverability and visualization.

Energy-based surgical instruments may be utilized in minimally-invasive surgical procedures to apply energy to target tissue within the internal body cavity to achieve a desired tissue effect. Gas-enhancement utilizes a gas (inert gas, energy-activated plasma, etc.) to displace fluid, disperse smoke, and/or facilitate the application of energy from the energy-based surgical instrument to tissue to achieve the desired tissue effect, and may likewise be utilized in a minimally-invasive surgical procedure.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a surgical system including a surgical instrument and a control assembly. The surgical instrument defines a gas inflow path, a gas outflow path, and an end effector configured to apply energy to tissue. The control assembly includes a gas output configured to connect to the gas inflow path of the surgical instrument for supplying gas thereto, a gas input configured to connect to the gas outflow path of the surgical instrument to withdraw gas therefrom, and an energy output configured to supply energy to the end effector of the surgical instrument for application to tissue. The control assembly further includes a controller having a processor and a non-transitory computer-readable storage medium storing instructions that, when executed, cause the processor to: determine an amount of gas output from the gas output to the gas inflow path of the surgical instrument, determine an amount of gas withdrawn into the gas input from the gas outflow path of the surgical instrument, compare the amount of gas output and the amount of gas withdrawn, and control withdrawal of gas from the gas outflow path of the surgical instrument such that the amount of gas output and the amount of gas withdrawn are equal to one another or within a threshold margin of one another.

In an aspect of the present disclosure, the control assembly includes a first pump configured to pump gas into the gas inflow path of the surgical instrument. Additionally or alternatively, the control assembly may include a second pump configured to withdraw gas from the gas outflow path of the surgical instrument.

In another aspect of the present disclosure, the control assembly includes a first sensor configured to sense at least one of: an output gas flow rate, an output gas pressure, or an output gas volume. In such aspects, the processor may further be caused to determine the amount of gas output from the gas output to the gas inflow path of the surgical instrument based upon feedback from the first sensor. Additionally or alternatively, the control assembly may include a second sensor configured to sense at least one of: an input gas flow rate, an input gas pressure, or an input gas volume. In such aspects, the processor may further be caused to determine the amount of gas withdrawn into the gas input from the gas outflow path of the surgical instrument based upon feedback from the second sensor.

In another aspect of the present disclosure, the control assembly is configured to supply gas from the gas output to the gas inflow path of the surgical instrument when the energy output supplies energy to the end effector of the surgical instrument for application to tissue.

Another surgical system provided in accordance with aspects of the present disclosure includes an electrode configured for insertion into an insufflated internal body cavity, a gas inflow path configured to extend into the insufflated internal body cavity, a gas outflow path configured to extend out of the insufflated internal body cavity, and a control assembly including an energy output configured to supply energy to the electrode, a gas output configured to supply gas along the gas inflow path into the insufflated internal body cavity when energy is supplied to the electrode, and a gas input configured to selectively withdrawn gas from the insufflated internal body cavity with the gas outflow path. The control assembly further includes a controller having a processor and a non-transitory computer-readable storage medium storing instructions that, when executed, cause the processor to: determine an amount of gas supplied into the insufflated internal body cavity, determine an amount of gas withdrawn from the insufflated internal body cavity, compare the amount of gas supplied and the amount of gas withdrawn, and control the withdrawal of gas from the insufflated internal body cavity such that the amount of gas supplied and the amount of gas withdrawn are equal to one another or within a threshold margin of one another.

In an aspect of the present disclosure, the electrode is disposed on a surgical instrument and the gas inflow and gas outflow paths are defined through the surgical instrument.

In another aspect of the present disclosure, the control assembly includes a first pump configured to supply gas and/or a second pump configured to withdraw gas.

In still another aspect of the present disclosure, the control assembly includes a first sensor configured to sense at least one of: a gas flow rate, a gas pressure, or a gas volume. In such aspects, the processor may further be caused to determine the amount of gas supplied based upon feedback from the first sensor.

In yet another aspect of the present disclosure, the control assembly includes a second sensor configured to sense at least one of: a gas flow rate, a gas pressure, or a gas volume. In such aspects, the processor may further be caused to determine the amount of gas withdrawn based upon feedback from the second sensor.

In still yet another aspect of the present disclosure, the control assembly is housed within an enclosure.

A method provided in accordance with aspects of the present disclosure includes inserting a surgical instrument into an insufflated internal body cavity, activating the surgical instrument to apply energy to tissue within the insufflated internal body cavity and introduce gas into the insufflated internal body cavity, determining an amount of gas that is introduced into the insufflated internal body cavity, and selectively withdrawing gas from the insufflated internal body cavity such that an amount of gas that is withdrawn is equal to or within a threshold margin of the amount of gas that is introduced.

In an aspect of the present disclosure, gas is provided from a control assembly to the surgical instrument for introduction into the insufflated internal body cavity. In such aspects, the control assembly may include a first sensor configured to sense at least one property indicative of the amount of gas that is introduced to enable determination of the amount of gas that is introduced.

In another aspect of the present disclosure, method according to claim 14, selectively withdrawing gas includes determining an amount of gas is withdrawn, comparing the amount of gas that is withdrawn with the amount of gas that is introduced, and determining whether to withdraw gas or not based upon a result of the comparison.

In yet another aspect of the present disclosure, gas is withdrawn from the insufflated internal body cavity into a control assembly. In such aspects, the control assembly may include a second sensor configured to sense at least one property indicative of the amount of gas that is withdrawn to enable determination of the amount of gas that is withdrawn.

Also provided in accordance with aspects of the present disclosure is a surgical instrument including a housing, an elongated shaft assembly extending distally from the housing, and an end effector extending distally from the elongated shaft assembly. The elongated shaft assembly includes an inner shaft, an intermediate collar, and an outer sleeve. The inner shaft defines a proximal portion, a distal portion, and a lumen extending longitudinally therethrough. The proximal portion of the inner shaft inhibits passage of gas radially therethrough, while the distal portion of the inner shaft permits passage of gas radially therethrough. The intermediate collar is disposed about the inner shaft between the proximal portion and the distal portion. The outer sleeve is disposed about the inner shaft and the intermediate collar. The outer sleeve is radially spaced-apart from the inner shaft and abuts an outer periphery of the intermediate collar to define a proximal annular area between the outer sleeve and the inner shaft proximally of the intermediate collar and a distal annular area between the outer sleeve and the inner shaft distally of the intermediate collar. The outer sleeve includes a proximal portion surrounding the proximal annular area and a distal portion surrounding the distal annular area. The proximal portion of the outer sleeve permits passage of gas radially therethrough, while the distal portion of the outer sleeve inhibits passage of gas radially therethrough.

In an aspect of the present disclosure, a distal cap encloses a distal end of the outer sleeve. In such aspects, the end effector may extend distally through the distal cap.

In another aspect of the present disclosure, the distal cap defines a plurality of openings in communication with the distal annular area to permit passage of gas from the distal annular area through the openings.

In still another aspect of the present disclosure, the plurality of openings are disposed radially about the end effector in a distally-oriented direction such that gas passing from the distal annular area through the openings is directed distally about the end effector.

In yet another aspect of the present disclosure, the distal portion of the inner shaft defines a plurality of transverse apertures therethrough to permit passage of gas radially therethrough from the lumen to the distal annular area.

In still yet another aspect of the present disclosure, the proximal portion of the outer sleeve defines a plurality of slots therethrough to permit passage of gas from an exterior of the outer sleeve radially therethrough into the proximal annular area.

In another aspect of the present disclosure, the end effector is engaged with the inner shaft at a distal end of the inner shaft and encloses the distal end of the inner shaft.

In yet another aspect of the present disclosure, the end effector includes an electrode adapted to connect to a source of energy for applying energy to tissue.

In another aspect of the present disclosure, the inner shaft is at least partially formed from an electrically-conductive material, disposed in electrical communication with the electrode, and adapted to deliver energy from a source of energy to the electrode for applying energy to tissue.

In still yet another aspect of the present disclosure, an inflow tube is disposed in communication with the lumen for supplying gas thereto and an outflow tube is disposed in communication with the proximal annular space for withdrawing gas therefrom.

Another surgical instrument provided in accordance with aspects of the present disclosure includes a housing, an elongated shaft assembly extending distally from the housing, and an end effector extending distally from the elongated shaft assembly. The elongated shaft assembly includes an inner shaft defining a lumen extending longitudinally therethrough, an outer sleeve disposed about and radially spaced-apart from the inner shaft to define an annular area therebetween, and an intermediate collar disposed between the inner shaft and the outer sleeve and dividing the annular area into a proximal annular area portion and a distal annular area portion. An inflow path is defined through the lumen, through openings defined within the inner shaft distally of the intermediate collar, through the distal annular area portion of the annular area, and through a distal end of the outer sleeve. An outflow path is defined through the proximal annular area portion and through openings defined within the outer sleeve proximally of the intermediate collar.

In an aspect of the present disclosure, the openings defined within the inner shaft distally of the intermediate collar are transverse apertures. Additionally or alternatively, the openings defined within the outer sleeve proximally of the intermediate collar may be longitudinally-extending slots.

In another aspect of the present disclosure, the elongated shaft assembly further includes a distal cap disposed at distal ends of the inner shaft and outer sleeve. In such aspects, the inflow path through the distal end of the outer sleeve may extend through openings defined within the distal cap.

In yet another aspect of the present disclosure, the end effector includes an electrode adapted to connect to a source of energy for applying energy to tissue.

In still another aspect of the present disclosure, the inner shaft is at least partially formed from an electrically-conductive material, disposed in electrical communication with the electrode, and adapted to deliver energy from a source of energy to the electrode for applying energy to tissue.

In still yet another aspect of the present disclosure, the outer sleeve is electrically-insulative.

In another aspect of the present disclosure, an inflow tube is disposed in communication with the inflow path for supplying gas thereto and an outflow tube is disposed in communication with the outflow path for withdrawing gas therefrom.

In another aspect of the present disclosure, at least one membrane is disposed about the openings defined within the outer sleeve proximally of the intermediate collar. The at least one membrane is configured to permit passage of gas therethrough and inhibit passage of liquid therethrough.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements and.

DETAILED DESCRIPTION

The present disclosure provides gas-enhanced energy-based surgical instruments, systems, and methods for use in minimally-invasive surgical procedures. Although the instruments, systems, and methods of the present disclosure are detailed herein configured for use in conjunction with one another, it is understood that the instruments, systems, and methods of the present disclosure also have applicability independently of one another and/or with other instruments, systems, and methods.

Figure 1:
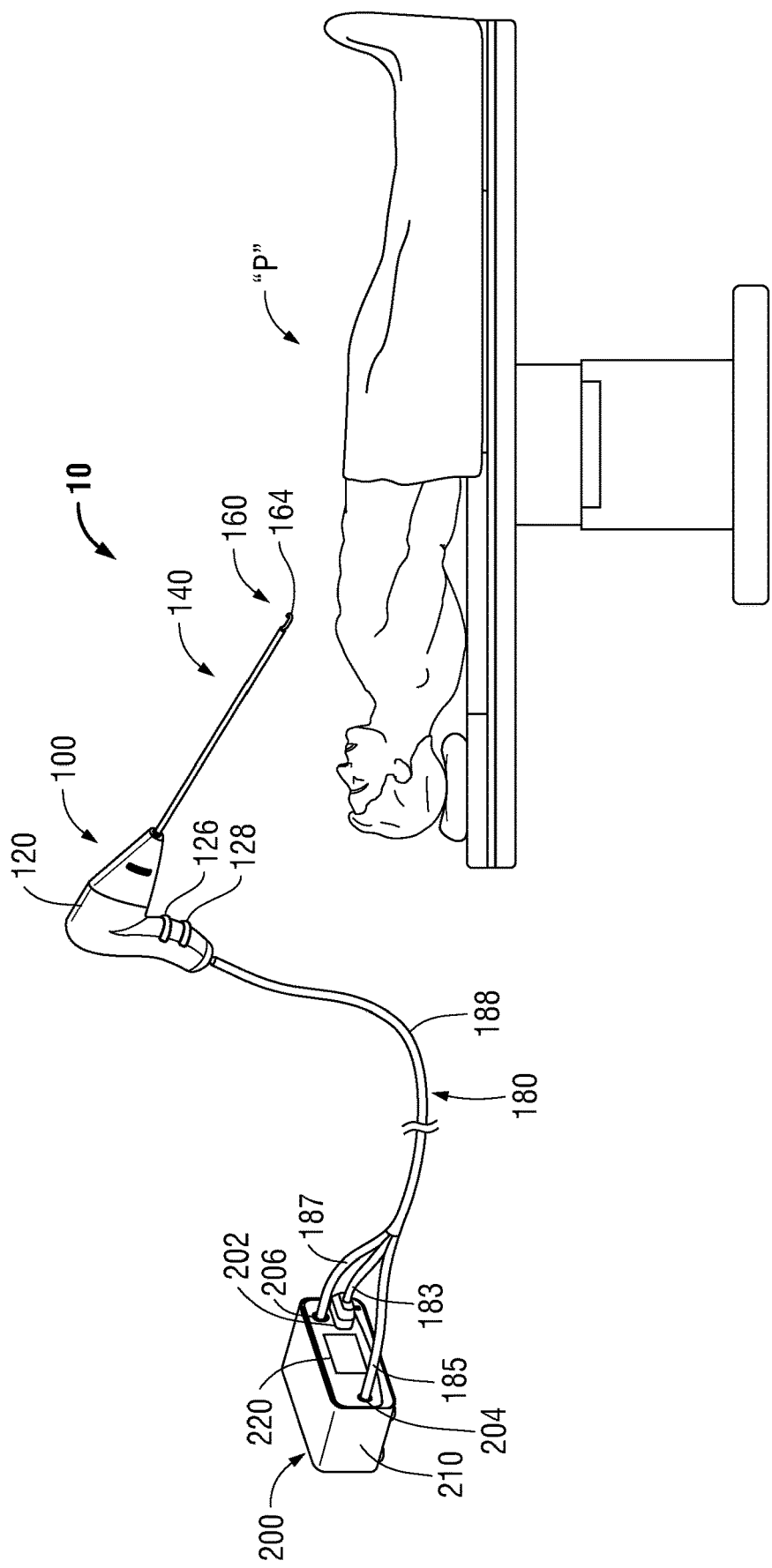
FIG. 1 is an illustration of a minimally-invasive, gas-enhanced, energy-based surgical system provided in accordance with the present disclosure shown in a surgical environment.
Figure 9:
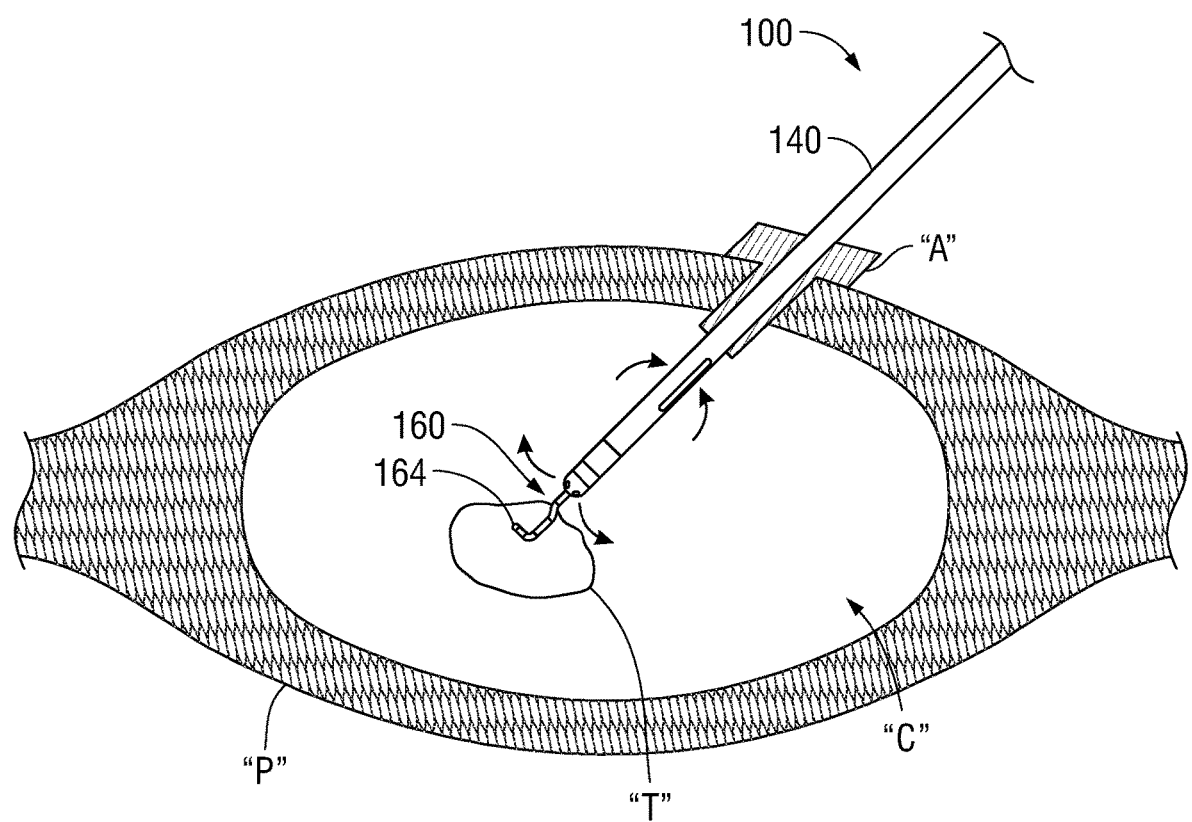
FIG. 9 is a perspective, partial cross-sectional view of the distal portion of the instrument of FIG. 2 in use within an internal body cavity.

Referring to FIG. 1, a gas-enhanced energy-based surgical system provided in accordance with the present disclosure is shown generally identified by reference numeral 10. System 10 includes a surgical instrument 100 and a control assembly 200 and is configured for use in minimally-invasive surgical procedures on a patient "P" within an insufflated internal body cavity "C" (FIG. 9) of the patient "P." Surgical instrument 100 is configured to supply energy, e.g., RF energy (although other energy modalities such as, for example, microwave, ultrasonic, laser, thermal, etc., are also contemplated), to tissue to achieve a desired tissue effect. Surgical instrument 100 is further configured to supply a gas, e.g., an inert gas, an energy-activated plasma, etc., at the site of energy application to facilitate achieving the desired tissue effect by, for example, displacing fluid, dispersing smoke, and/or facilitating the application of energy to tissue. Surgical instrument 100 is also configured to withdraw gas from the insufflated internal body cavity "C" (FIG. 9) to maintain an appropriate insufflation pressure within the insufflated internal body cavity "C" (FIG. 9). Surgical instrument 100 is described in greater detail below.

Control assembly 200 of system 10 may be configured as a single unit housed within an enclosure 210 (as illustrated in FIG. 1) or may include several sub-units operably coupled to one another (in close proximity or remote from one another). Control assembly 200 is coupled to surgical instrument 100 and is configured to supply and control the supply of energy to tissue via surgical instrument 100, supply and control the supply of gas to the site of energy application via surgical instrument 100, and withdraw and control the withdrawal of gas from the insufflated internal body cavity "C" (FIG. 9) via surgical instrument 100. Control assembly 200 is described in greater detail below.

Figure 2:
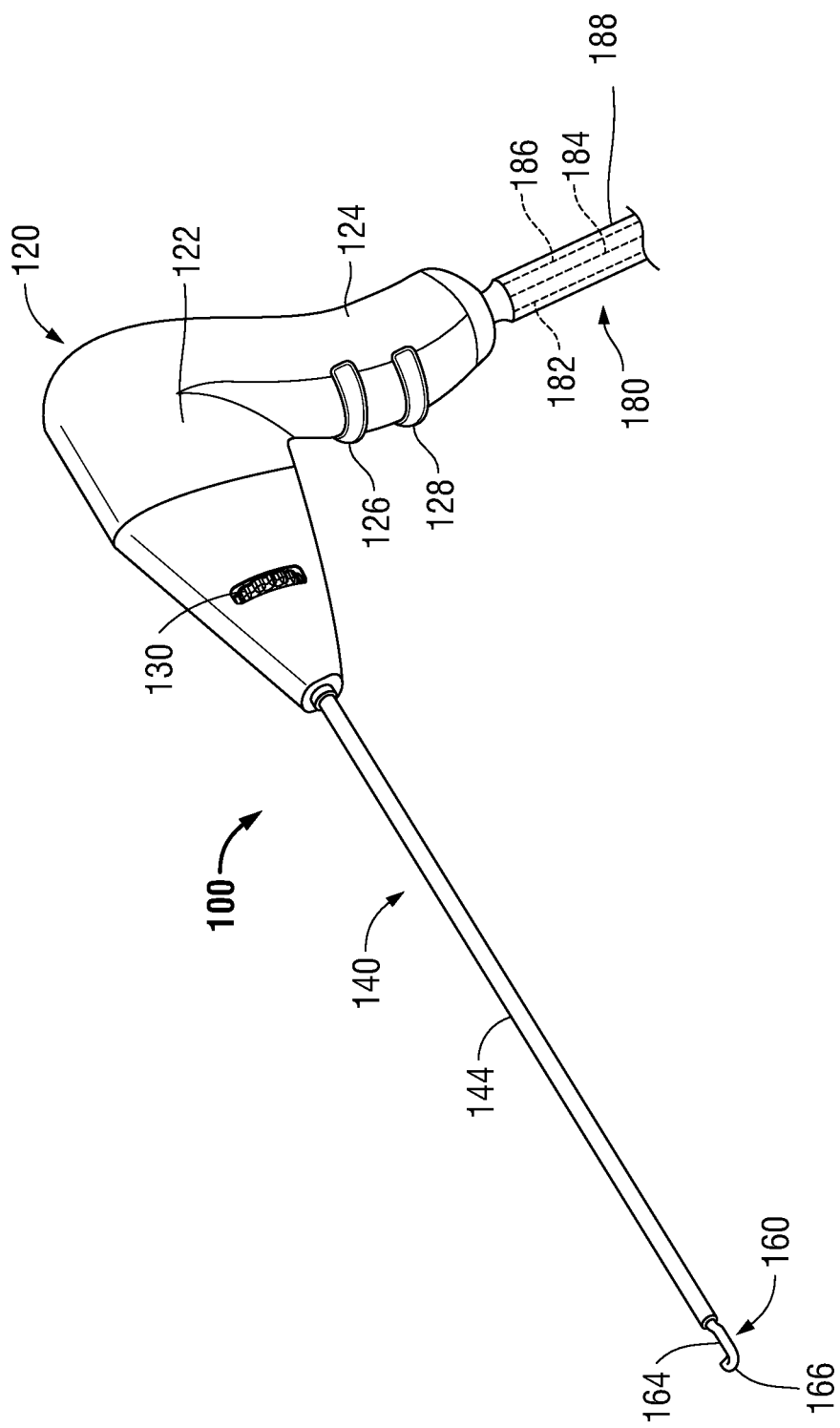
FIG. 2 is a perspective view of a surgical instrument of the system of FIG. 1.

Turning to FIGS. 2-6, and initially to FIG. 2, surgical instrument 100 generally includes a housing 120, an elongated shaft assembly 140 extending distally from housing 120, an end effector 160 extending distally from elongated shaft assembly 140, and a connection assembly 180 operably coupled to housing 120 and configured to operably connect surgical instrument 100 to control assembly 200 (FIG. 1). Surgical instrument 100 may be configured as a disposable, single-use instrument; a reusable, multi-use instrument capable of being sterilized for repeated use; or a reposable instrument wherein some portions are capable of being sterilized for repeated use and other portions are disposable, single-use portions that are replaced after each use.

Continuing with reference to FIG. 2, housing 120 includes a body portion 122 an a fixed handle portion 124 extending perpendicularly or obliquely from body portion 122 to provide an ergonomic pistol-grip configuration facilitating grasping and manipulating housing 120, although other suitable configurations, e.g., a pencil-grip configuration, are also contemplated. Housing 120 further includes an energy activation button 126, a gas supply activation button 128, and a rotation wheel 130, although additional or alternative controls are also contemplated.

With reference to FIGS. 3-6, elongated shaft assembly 140, as noted above, extends distally from housing 120 (FIG. 2). A proximal portion (not shown) of elongated shaft assembly 140 is disposed within housing 120 and operably coupled to rotation wheel 130 (FIG. 2) within housing 120 to enable rotation of elongated shaft assembly 140 relative to housing 120 in response to rotation of rotation wheel 130 relative to housing 120. Elongated shaft assembly 140 extends from the proximal portion thereof, distally from housing 120, to end effector 160.

Figure 4:
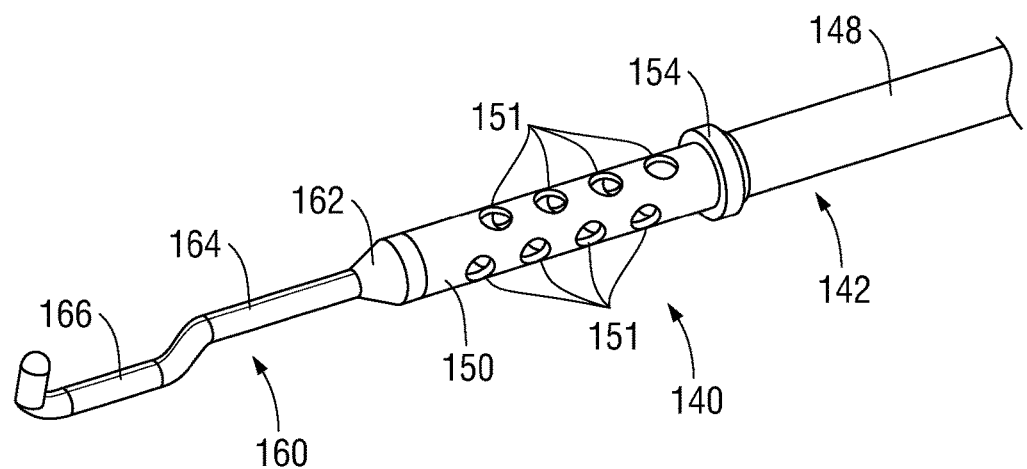
FIG. 4 is a perspective view of the distal portion of the instrument of FIG. 2 with the outer sleeve and distal cap removed.
Figure 5:
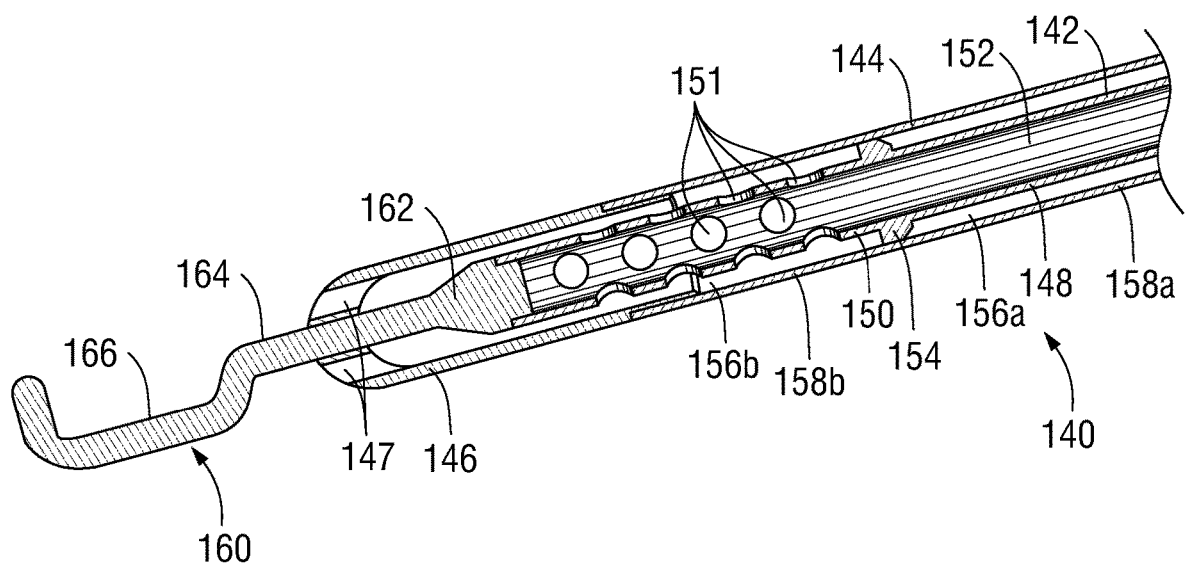
FIG. 5 is an enlarged, perspective, longitudinal cross-sectional view of the area of detail indicated as "5" in FIG. 3.

Elongated shaft assembly 140 includes an inner shaft 142, an outer sleeve 144, and a distal cap 146. Referring to FIGS. 4 and 5, inner shaft 142 is formed at least partially from an electrically-conductive material, includes a proximal portion 148 and a distal portion 150 (of similar or different length), and defines a longitudinally-extending lumen 152 therethrough. An intermediate collar 154 is disposed about inner shaft 142 between proximal portion 148 and a distal portion 150 thereof. Proximal portion 148 of inner shaft 142 defines a solid outer annular surface; that is, proximal portion 148 of inner shaft 142 is configured to inhibit the passage of gas between lumen 152 and the radial exterior of proximal portion 148 of inner shaft 142. Distal portion 150 of inner shaft 142, defines a plurality of transverse apertures 151 therethrough arranged annularly about and longitudinally along at least a portion thereof in any suitable arrangement and/or pattern. Apertures 151 enable the passage of gas radially between lumen 152 and the exterior of distal portion 150 of inner shaft 142.

Figure 3:
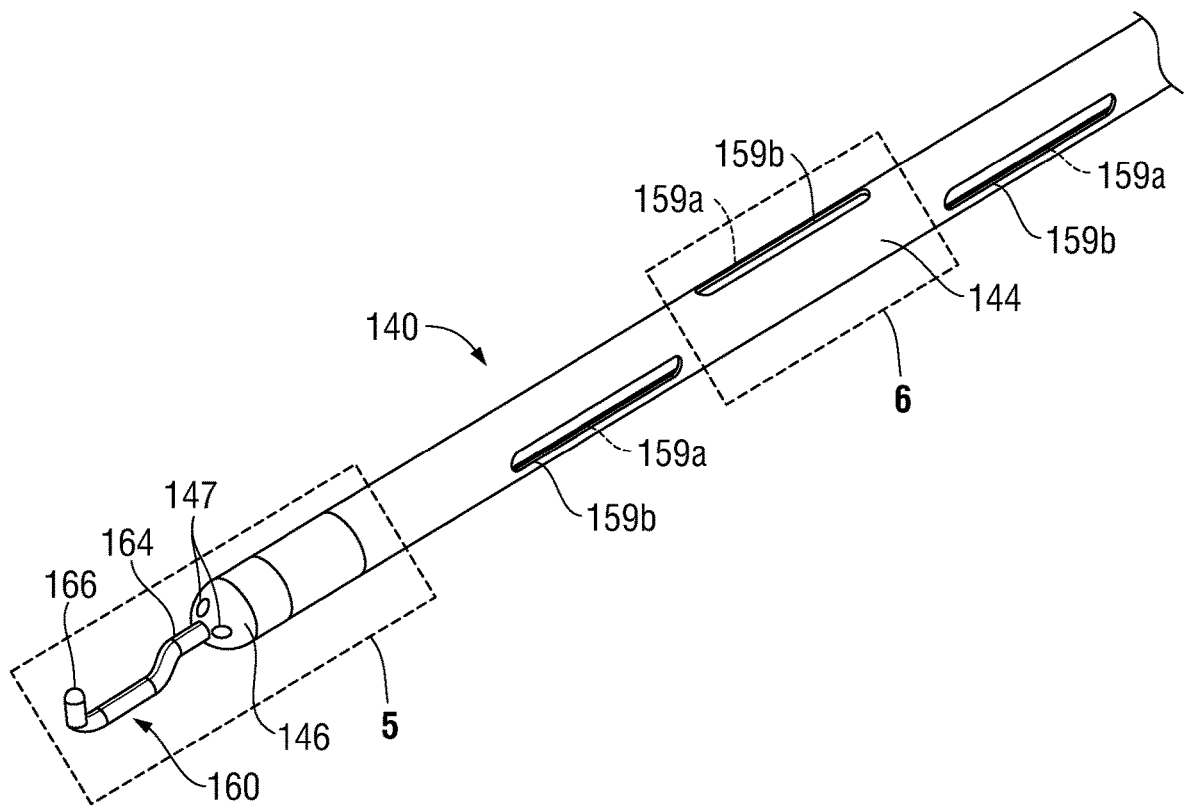
FIG. 3 is a perspective view of a distal portion of the instrument of FIG. 2.
Figure 6:
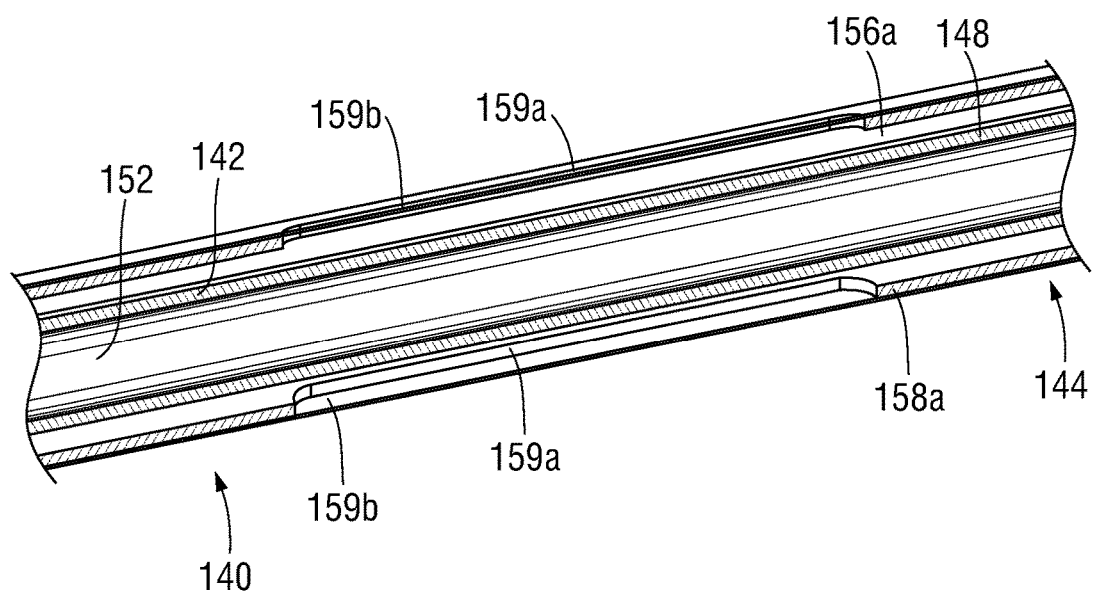
FIG. 6 is an enlarged, perspective, longitudinal cross-sectional view of the area of detail indicated as "6" in FIG. 3.
Figure 7:
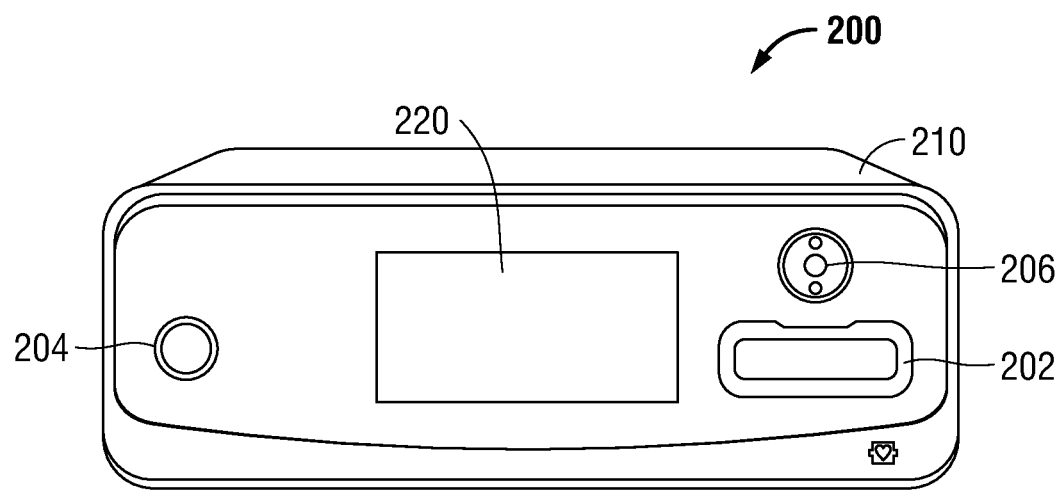
FIG. 7 is a perspective view of a control assembly of the system of FIG. 1.

Referring to FIGS. 3, 5, and 6, outer sleeve 144 of elongated shaft assembly 140 is formed from an electrically-insulative material, coated with an electrically-insulated material, or otherwise configured to inhibit the conduction of electrical energy therethrough. In embodiments, outer sleeve 144 is formed from, for example, woven carbon fiber or a biocompatible polymer. Outer sleeve 144 is disposed about and radially-spaced from inner shaft 142 of elongated shaft assembly 140 to define a proximal annular space 156a between outer sleeve 144 and proximal portion 148 of inner shaft 142 and a distal annular space 156b between outer sleeve 144 and distal portion 150 of inner shaft 142. Outer sleeve 144 abuts the outer radial surface of intermediate collar 154 to establish a seal therebetween to inhibit gas exchange between proximal annular space 156a and distal annular space 156b. The abutment of outer sleeve 144 with intermediate collar 154 also serves to maintain inner shaft 142 in concentric position within outer sleeve 144, thus maintaining proximal and distal annular spaces 156a, 156b, respectively, between inner shaft 142 and outer sleeve 144.

Outer sleeve 144 includes a proximal portion 158a surrounding proximal annular space 156a and a distal portion 158b surrounding distal annular space 156b. Proximal portion 158a of outer sleeve 144 defines a plurality of longitudinally-extending slots 159a therethrough arranged annularly about and longitudinally along at least a portion thereof in any suitable arrangement and/or pattern. Slots 159a enable the passage of gas radially between proximal annular space 156a and the exterior of proximal portion 158a of outer sleeve 144. Distal portion 158b of outer sleeve 144, on the other hand, defines a solid outer annular surface; that is, distal portion 158b of outer sleeve 144 is configured to inhibit the passage of gas between distal annular space 156b and the radial exterior of distal portion 158b of outer sleeve 144.

Outer sleeve 144, in embodiments, may further include one or more membranes 159b disposed at least about slots 159a. Each membrane 159b may be a hydrophobic membrane or other suitable membrane that enables the exchange of gas therethrough but inhibits the exchange of liquids therethrough. Suitable membranes include, for example, microporous PTFE and GOR-TEX®, available from W.L. Gore & Associates GmbH.

Referring to FIGS. 3 and 5, distal cap 146 of elongated shaft assembly 140 is disposed at the distal ends of inner shaft 142 and outer sleeve 144 and may define a semispherical configuration (as illustrated), a frustoconical configuration, or other suitable configuration. Distal cap 146 encloses the distal end of distal annular space 156b and defines a plurality of radially-arranged apertures 147 defined therethrough and oriented in a generally distally-facing direction. Apertures 147 thus enable gas disposed within distal annular space 156b to exit surgical instrument 100 through apertures 147 in a distal direction radially about end effector 160, as detailed below.

Continuing with reference to FIGS. 3 and 5, end effector 160 includes a hub 162 and an electrode 164 extending distally from hub 162. Hub 162 is engaged, e.g., welded, with distal portion 150 of inner shaft 142 at the distal end of distal portion 150 to seal off the distal end of lumen 152. Hub 162 is formed at least partially from an electrically-conductive material and is electrically coupled to inner shaft 142, e.g., via direct mechanical contact therebetween. Electrode 164 is likewise formed at least partially from an electrically-conductive material and extends distally from hub 162. Electrode 164 may be engaged with, monolithically formed with, or otherwise coupled to hub 162 in electrical communication therewith. End effector 160 is fixed relative to elongated shaft assembly 140 such that end effector 160 is rotated in conjunction with elongated shaft assembly 140 and relative to housing 120 (FIG. 2), e.g., in response to rotation of rotation wheel 130 relative to housing 120 (see FIG. 2).

Electrode 164, as noted above, extends distally from hub 162. More specifically, electrode 164 extends distally through a central opening defined through distal cap 146 and distally of elongated shaft assembly 140. Electrode 164 fully occupies the central opening of distal cap 146 or is otherwise sealed therein to inhibit the passage of gas through the central opening between electrode 164 and distal cap 146. Electrode 164 is also radially surrounded by and extends distally from apertures 147 of distal cap 146. As such, gas exiting elongated shaft assembly 140 distally through apertures 147 is directed radially about electrode 164 and distally towards the distal-most end of electrode 164. Electrode 164 may define a distal portion 166 having any suitable configuration to facilitate communicating energy to tissue such as, for example, a hook-shape (as illustrated) or other suitable shape.

With reference back to FIGS. 1 and 2, connection assembly 180 of surgical instrument 100 includes a cable 182, and inflow tube 184, and an outflow tube 186 disposed within an outer sheath 188, although cable 182, inflow tube 184, and/or outflow tube 186 may alternatively be connected to one another without an outer cable sheath, may be separate from one another, or may be configured in any other suitable manner. Cable 182 includes a plug 183 at the proximal end thereof configured to connect surgical instrument 100 to an energy output 202 of control assembly 200. Cable 182 extends distally through outer sheath 188 into housing 120, wherein a lead wire (not explicitly show) extending through cable 182 is electrically connected to inner shaft 142 of elongated shaft assembly 140, e.g., via a slip-ring connection (not shown). Thus, energy, e.g., RF energy, may be delivered from control assembly 200 to electrode 164 via the lead wire of cable 182 and inner shaft 142 for application to tissue to achieve a desired tissue effect. Cable 182 may additionally house one or more control wires (not explicitly shown) configured to connect energy activation button 126 and/or gas supply activation button 128 to control assembly 200 to enable the selective activation of energy and/or gas supply from control assembly 200 to surgical instrument 100.

Inflow tube 184 of connection assembly 180 includes a plug 185 at the proximal end thereof configured to connect surgical instrument 100 to a gas output 204 of control assembly 200. Inflow tube 184 extends distally through outer sheath 188 into housing 120, wherein the distal end of inflow tube 184 is disposed in communication with lumen 152 of inner shaft 142 in sealed relation. Thus, gas, e.g., an inert gas such as $CO_2$, may be delivered from control assembly 200 to lumen 152 via inflow tube 184. More specifically, gas may be pumped through inflow tube 184 and lumen 152, exiting lumen 152 and entering distal annular space 156b via transverse apertures 151 defined within distal portion 150 of inner shaft 142, and exiting distal annular space 156b through apertures 147 of distal cap 146 such that the gas is expelled distally into the internal body cavity "C" (FIG. 9) about electrode 164 to facilitate achieving the desired tissue effect, e.g., via displacing fluid, dispersing smoke, and/or facilitating the application of energy from electrode 164 to tissue.

Outflow tube 186 of connection assembly 180 includes a plug 187 at the proximal end thereof configured to connect surgical instrument 100 to a gas input 206 of control assembly 200. Outflow tube 186 extends distally through outer sheath 188 into housing 120, wherein the distal end of outflow tube 184 is disposed in communication with proximal annular space 156a defined between inner shaft 142 and outer sleeve 144, in sealed relation. Thus, gas may be draw from the internal body cavity "C" (FIG. 9) into proximal annular space 156a via slots 159a (and through membrane(s) 159b) of outer sleeve 144, proximally through proximal annular space 156a, into and through outflow tube 186, and, ultimately, to control assembly 200 for collection, recycling, exhausting, etc.

Referring generally to FIGS. 1-6 and 9, end effector 160 and elongated shaft assembly 140 of surgical instrument 100 are configured for minimally-invasive insertion into an insufflated internal body cavity "C," e.g., through an access port "A," while housing 120 of surgical instrument 100 remains externally disposed to enable manipulation and/or activation of surgical instrument 100. Once inserted in this manner, surgical instrument 100 may be activated to supply energy to tissue "T" via electrode 164, supply a gas about electrode 164 adjacent tissue "T" to facilitate achieving a desired tissue effect, and withdraw gas from the insufflated internal body cavity "C" (while, in embodiments, also inhibiting the withdrawal of liquids from the insufflated internal body cavity "C") at positions proximally-spaced from electrode 164 and tissue "T" so as not to interfere with the application of energy to tissue and/or the supplied input gas.

Turning to FIGS. 1 and 7-9, control assembly 200, as noted above, includes energy output 202 configured to supply energy to surgical instrument 100, a gas output 204 configured to supply gas to surgical instrument 100, and a gas input 206 configured to withdraw gas from surgical instrument 100. Control assembly 200, as also noted above, may be housed within a single enclosure 210 (as shown) or may be a combination of sub-assemblies coupled to one another. Enclosure 210 (and/or one or more of the sub-assemblies, in embodiments where provided) may further include a display screen 220, which may be a touch-screen display to enable input as well as to provide a visual output. Other input and/or output components are also contemplated such as, for example, speakers, LEDs, keypads, etc.

Figure 8:
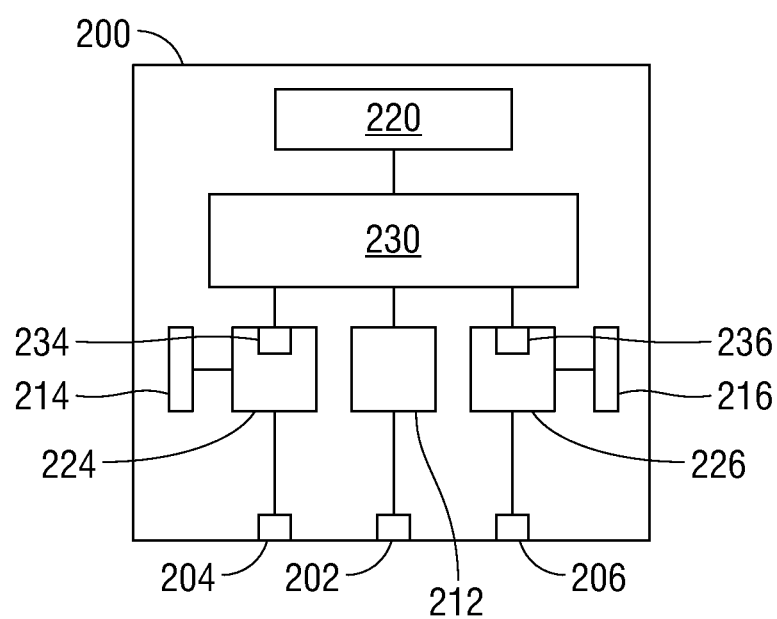
FIG. 8 is a schematic diagram of the control assembly of FIG. 7.

With particular reference to FIG. 8, control assembly 200 further includes an RF generator 212 configured to convert power, e.g., from a wall outlet (not shown), into electrosurgical RF energy for output to energy output 202 such that RF energy may be delivered from control assembly 200 to electrode 164 of surgical instrument 100 (see FIG. 1) for application to tissue "T" (FIG. 9). Control assembly 200 also includes or is coupled to a gas source 214 and a pump 224 coupled between gas source 214 and gas output 204 to enable gas to be pumped from gas source 214 through surgical instrument 100 and into the internal body cavity "C" about end effector 160 (see FIG. 9), as detailed above. Control assembly 200 additionally includes or is coupled to a gas reservoir 216 and a pump 226 coupled between gas reservoir 216 and gas input 206 to enable gas to be withdrawn, e.g., suctioned, from the internal body cavity "C" via instrument 100 (see FIG. 9), as detailed above, for depositing in gas reservoir 216.

Referring again to FIGS. 1 and 7-9, control assembly 200 also includes a controller 230 including, for example, a microcontroller and a storage medium storing instructions to be executed by the microcontroller. Controller 230 is configured to receive input information from surgical instrument 100, e.g., activation signals from energy activation button 126 and/or gas supply activation button 128, and direct an appropriate output, e.g., the supply of energy to electrode 164 or the output of gas to surgical instrument 100. Controller 230 may be configured to automatically output gas to surgical instrument 100 when energy is supplied to surgical instrument 100 (concurrently or delayed relative thereto) and/or may be configured to output gas to surgical instrument 100 in response to activation of gas supply activation button 128.

Controller 230 is further configured to monitor the amount, e.g., volume, of gas output to surgical instrument 100 and, thus, the amount of gas input into the internal body cavity "C." This may be accomplished using a sensor 234 configured to sense a flow rate of gas output via pump 224 (or at any other suitable location) such that, knowing the dimensions of the components within the gas output flow path, controller 230 can determine the amount of gas input into the internal body cavity "C." Alternatively, sensor 234 may be configured to sense a pressure and/or volume difference within gas source 214 such that controller 230 can correlate the same to the amount of gas pumped into the internal body cavity "C." As another alternative, sensor 234 may be configured to monitor the power consumption, torque, impedance, and/or other suitable parameter(s) of pump 224 and correlate the same to an amount to enable controller 230 to determine the amount of gas pumped to surgical instrument 100 and, thus, the amount of gas input into the internal body cavity "C." As still another alternative, sensor 234 may be configured to monitor the "ON" time of pump 224 such that controller 230, knowing the output of pump 224, can determine the amount of gas input into the internal body cavity "C." Other suitable configurations of sensor 234 for determining the amount of gas input into the internal body cavity "C" are also contemplated. The amount of gas input into the internal body cavity "C" is stored in a memory of controller 230 and updated continuously or periodically.

Continuing with reference to FIGS. 1 and 7-9, controller 230 is also configured to control pump 226, thereby controlling the withdrawal of gas from the internal body cavity "C" via instrument 100, for ultimate depositing in gas reservoir 216. More specifically, controller 230 is configured to control the withdrawal of gas from the internal body cavity "C" in accordance with the determined amount of gas input into the internal body cavity "C" such that the amount of gas withdrawn is equal to or within a threshold margin of the amount of gas input. The threshold margin may be an absolute value, e.g., a numerical volume, or a relative value, e.g., a percentage of the input volume. As such, the amount of gas within the insufflated internal body cavity "C" (absent other factors contributing to the addition or loss of gas) is maintained constant or within a threshold range throughout use of surgical instrument 100. Thus, the pressure within the insufflated internal body cavity "C" (absent other factors contributing to the addition or loss of pressure) is also maintained constant or within a threshold range throughout use of surgical instrument 100.

Controller 230 controls the withdrawal of gas from the internal body cavity "C," in embodiments, by monitoring the amount of gas withdrawn from the internal body cavity "C," comparing the amount of gas withdrawn to the amount of gas input (stored in the memory of controller 230), and selectively operating pump 226 to ensure the amount of gas withdrawn is equal to or within a threshold margin of the amount of gas input. Controller 230 may utilize a sensor 236 such as, for example, a flow rate sensor, a pressure and/or volume sensor, a pump parameter sensor, an "ON" time sensor, etc. (similarly as detailed above with respect to sensor 234), to determine the amount of gas withdraw from the internal body cavity "C." Controller 230 may compare the determined input and withdrawn amounts continuously or periodically, and automatically control activation (and deactivation) of pump 226 to withdraw gas as necessary to ensure that the amount of gas and/or pressure within the insufflated internal body cavity "C" (absent other factors) is maintained constant or within a threshold range throughout use of surgical instrument 100.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
    a housing;
    an elongated shaft assembly extending distally from the housing, the elongated shaft assembly including:
        an inner shaft defining a proximal portion, a distal portion, and a lumen extending longitudinally therethrough, the proximal portion of the inner shaft inhibiting passage of gas radially therethrough, the distal portion of the inner shaft defining at least one opening permitting passage of the gas radially therethrough;
        an intermediate collar disposed about the inner shaft between the proximal portion and the distal portion; and
        an outer sleeve disposed about and fixed relative to the inner shaft and the intermediate collar, the outer sleeve radially spaced-apart from the inner shaft, wherein the intermediate collar establishes an annular seal between the outer sleeve and the inner shaft to define a proximal annular area between the outer sleeve and the inner shaft proximally of the intermediate collar and a distal annular area between the outer sleeve and the inner shaft distally of the intermediate collar, the annular seal inhibiting gas exchange between the proximal annular area and the distal annular area, the outer sleeve including a proximal portion surrounding the proximal annular area and a distal portion surrounding the distal annular area, the proximal portion of the outer sleeve defining at least one opening permitting passage of the gas radially therethrough, the distal portion of the outer sleeve inhibiting passage of the gas radially therethrough; and
    an end effector extending distally from the elongated shaft assembly.

2. The surgical instrument according to claim 1, further comprising a distal cap enclosing a distal end of the outer sleeve, wherein the end effector extends distally through the distal cap.

3. The surgical instrument according to claim 2, wherein the distal cap defines a plurality of openings in communication with the distal annular area to permit passage of the gas from the distal annular area through the plurality of openings.

4. The surgical instrument according to claim 3, wherein the plurality of openings are disposed radially about the end effector in a distally-oriented direction such that the gas passing from the distal annular area through the plurality of openings is directed distally about the end effector.

5. The surgical instrument according to claim 1, wherein the at least one opening of the distal portion of the inner shaft includes a plurality of transverse apertures to permit passage of the gas radially therethrough from the lumen to the distal annular area.

6. The surgical instrument according to claim 1, wherein the at least one opening of the proximal portion of the outer sleeve includes a plurality of slots to permit passage of the gas from an exterior of the outer sleeve radially therethrough into the proximal annular area.

7. The surgical instrument according to claim 1, wherein the end effector is engaged with the inner shaft at a distal end of the inner shaft and encloses the distal end of the inner shaft.

8. The surgical instrument according to claim 1, wherein the end effector includes an electrode adapted to connect to a source of energy for applying the energy to tissue.

9. The surgical instrument according to claim 8, wherein the inner shaft is at least partially formed from an electrically-conductive material, disposed in electrical communication with the electrode, and adapted to deliver the energy from the source of energy to the electrode for applying the energy to tissue.

10. The surgical instrument according to claim 1, further comprising:
    an inflow tube in communication with the lumen for supplying the gas thereto; and
    an outflow tube in communication with the proximal annular area for withdrawing the gas therefrom.

11. A surgical instrument, comprising:
    a housing;
    an elongated shaft assembly extending distally from the housing, the elongated shaft assembly including:
        an inner shaft defining a lumen extending longitudinally therethrough;

an outer sleeve disposed about, fixed relative to, and radially spaced-apart from the inner shaft to define an annular area therebetween; and an intermediate collar establishing an annular seal between the inner shaft and the outer sleeve to divide the annular area into a proximal annular area portion and a distal annular area portion and inhibit gas exchange between the proximal annular area portion and the distal annular area portion, wherein the outer sleeve defines at least one opening permitting passage of gas radially therethrough and into the proximal annular area portion and inhibits passage of the gas radially therethrough and into the distal annular area portion, and wherein the inner shaft inhibits passage of the gas radially therethrough and into the proximal annular area portion and defines at least one opening permitting passage of the gas radially therethrough and into the distal annular area portion, such that:

an inflow path is defined through the lumen, through the at least one opening defined within the inner shaft distally of the intermediate collar, through the distal annular area portion of the annular area, and through a distal end of the outer sleeve, and an outflow path is defined through the proximal annular area portion and through the at least one opening defined within the outer sleeve proximally of the intermediate collar; and an end effector extending distally from the elongated shaft assembly.

12. The surgical instrument according to claim 11, wherein the at least one opening defined within the inner shaft distally of the intermediate collar includes at least one transverse aperture.

13. The surgical instrument according to claim 11, wherein the at least one opening defined within the outer sleeve proximally of the intermediate collar includes at least one longitudinally-extending slot.

14. The surgical instrument according to claim 11, wherein the elongated shaft assembly further includes a distal cap disposed at a distal end of the inner shaft and the distal end of the outer sleeve.

15. The surgical instrument according to claim 14, wherein the inflow path through the distal end of the outer sleeve extends through openings defined within the distal cap.

16. The surgical instrument according to claim 11, wherein the end effector includes an electrode adapted to connect to a source of energy for applying the energy to tissue.

17. The surgical instrument according to claim 16, wherein the inner shaft is at least partially formed from an electrically-conductive material, disposed in electrical communication with the electrode, and adapted to deliver the energy from the source of energy to the electrode for applying the energy to tissue.

18. The surgical instrument according to claim 17, wherein the outer sleeve is electrically-insulative.

19. The surgical instrument according to claim 11, further comprising:
 an inflow tube in communication with the inflow path for supplying the gas thereto; and
 an outflow tube in communication with the outflow path for withdrawing the gas therefrom.

20. The surgical instrument according to claim 11, further comprising at least one membrane disposed about the openings defined within the outer sleeve proximally of the intermediate collar, the at least one membrane configured to permit passage of the gas therethrough and inhibit passage of liquid therethrough.

* * * * *